United States Patent [19]

Matsuura et al.

[11] 4,257,851
[45] Mar. 24, 1981

[54] PURIFICATION OF NAPHTHOQUINONE

[75] Inventors: Ryo Matsuura, Yamato; Kazuaki Sakai, Fujisawa; Tuneyasu Sato, Chigasaki; Yorinobu Yamada; Kowzo Bandow, both of Kawasaki, all of Japan

[73] Assignee: Kawasaki Kasei Chemicals Ltd., Tokyo, Japan

[21] Appl. No.: 22,878

[22] Filed: Mar. 22, 1979

[30] Foreign Application Priority Data

Mar. 27, 1978 [JP] Japan .................................. 53-35825
Apr. 26, 1978 [JP] Japan .................................. 53-49466

[51] Int. Cl.³ .......................... B01D 3/10; C07C 50/00
[52] U.S. Cl. ......................................... 203/31; 203/33; 203/34; 203/38; 203/43; 203/91; 260/396 R
[58] Field of Search ............... 260/396 R; 203/91, 31, 203/33, 36, 37, 38, 43, 95, 39

[56] References Cited

U.S. PATENT DOCUMENTS

| 2,536,833 | 1/1951 | Bailey | 260/396 R |
| 2,779,722 | 1/1957 | Murray et al. | 203/31 |
| 3,441,576 | 4/1969 | Berndtsson | 260/396 R |

OTHER PUBLICATIONS

Chem. Abstracts 66 (1967) 2309k.
Chem. Abstracts 60 (1964) 1662d.

Primary Examiner—Wilbur L. Bascomb, Jr.
Attorney, Agent, or Firm—Oblon, Fisher, Spivak, McClelland & Maier

[57] ABSTRACT

A crude naphthoquinone produced by an oxidation of naphthalene is purified by a reduced pressure distillation of a crude 1,4-naphthoquinone having an acid content of less than 5 equivalent % calculated as monobasic acid and the crude naphthoquinone is preferably treated by an oxidation of oxidizable impurities.

9 Claims, 2 Drawing Figures

PURIFICATION OF NAPHTHOQUINONE

BACKGROUND OF THE INVENTION

1. Field of the Invention

The present invention relates to a process for purifying a crude 1,4-naphthoquinone (hereinafter referring to as naphthoquinone) obtained by an oxidation of naphthalene.

2. Description of the Prior Arts

Heretofore, naphthoquinone especially 1,4-naphthoquinone has been produced by an oxidation of naphthalene, for example, by a process for oxidizing naphthalene in liquid phase with an oxidizing agent such as hydrogen peroxide in the presence of boric acid or a process for oxidizing naphthalene by a catalytic vapor phase oxidization. However, large amount of impurities such as acidic impurities and polycondensed impurities have been produced together with naphthoquinone in these processes whereby a highly purified naphthoquinone could not be easily obtained.

In the conventional catalytic vapor phase oxidation of naphthalene, a reaction mixture gas (naphthoquinone, phthalic anhydride, maleic anhydride, and naphthalene) produced by an oxidation of naphthalene, is trated with water to collect naphthoquinone and impurities of phthalic anhydride and maleic anhydride, with or without condensing phthalic anhydride in a pretreatment, and then, naphthoquinone is separated from water soluble impurities of phthalic acid and maleic acid, etc. to obtain naphthoquinone in an industrial process.

However, the resulting crude naphthoquinone usually contains impurities of phthalic acid, benzoic acid, maleic acid and polycondensed naphthoquinone materials derived from naphthoquinone.

A highly purified naphthoquinone has been obtained by the methods such as sublimation method, solvent extraction method and recrystallization method. However, the solvent extraction method and the recrystallization method suffer such disadvantages that highly purified naphthoquinone is not easily obtained by recrystallization and use of large volume of an organic solvent as a recrystallizing solvent is particularly dangerous, because of its firing and toxicity in the industry and the yield is usually very poor. On the other hand, the sublimation method has been industrially employed however, a thermal polycondensation of a crude naphthoquinone is easily casued and accordingly, the sublimation method should be carried out in a fluidized bed process carrying naphthoquinone with a large amount of air etc. below the melting temperature of naphthoquinone (Japanese Patent Publication No. 23013/1965 and W. Ger. Pat. No. 1,232,943). However, these conventional sublimation method suffers such disadvantages that (1) efficiency of an equipment is low and heat loss is large, because of its low vapor density, (2) the possibility of firing and explosion is present because of using large volume of air, which is very cheap, and (3) it is very difficult to obtain a highly purified naphthoquinone only by this method.

On the contrary, a distillation method has many disadvantages in an industrial process that (1) the carrier gas such as air does not need to be used because of its high vapor density and (2) a compact plant is possible to be used because of its high heat transfer. Nevertheless, the distillation method has not been used to get highly purified naphthoquinone because a polycondensation reaction of naphthoquinone easily occurs to get a pitch at the temperature higher than its melting point.

SUMMARY OF THE INVENTION

It is an object of the present invention to provide a process for purifying a crude naphthoquinone by a reduced pressure distillation without causing a polycondensation of naphthoquinone even though it is heated at the higher temperature than its melting point.

It is the other object of the present invention to obtain a highly purified naphthoquinone in high yield and high efficiency without causing a polycondensation even though the crude naphthoquinone is heated at the temperature higher than its melting point.

The foregoing and other objects of the present invention have been attained by purifying a crude naphthoquinone obtained by an oxidation of naphthalene by a reduced pressure distillation of a crude naphthoquinone having an acid content of less than 5 equivalent % calculated as monobasic acid. It is preferable to oxidize oxidizable impurities in the crude naphthoquinone before the reduced pressure distillation.

DETAILED DESCRIPTION OF THE PREFERRED EMBODIMENTS

In the reduced pressure distillation for the purification of the present invention, the crude naphthoquinone should have an acid content of less than 5 equivalent % preferably less than 3 equivalent % calculated as monobasic acid.

The acid components include organic acids such as phthalic acid, maleic acid and benzoic acid. Maleic acid is water soluble and accordingly it can be easily removed by washing with water.

Inorganic acids such as sulfuric acid may be included. Sulfuric acid can be separated in the oxidation of naphthalene, especially in a step of separating naphthoquinone in the case of the catalytic vapor phase oxidation. Therefore, sulfuric acid may not be remained as the acid component. However, when such strong acids are remained, they should be removed by washing with water.

In the process of the present invention, the crude naphthoquinone having an acid content of less than 5 equivalent % calculated as carboxyl group based on naphthoquinone is obtained by reducing content of organic acids especially phthalic acid and bezoic acid to attain the object of the present invention.

When the acid component is phthalic acid or benzoic acid, the content of the acid component should be less than about 2.5 wt.% of phthalic acid or less than about 3.7 wt.% of benzoic acid in the case of 95% crude naphthoquinone or less than about 2.4 wt.% of phthalic acid or less than about 3.5 wt.% of benzoic acid in the case of 90% crude naphthoquinone. The acid content should be reduced in said level by treating the crude naphthoquinone.

It has been investigated in detail how the presence of acidic material influences the polycondensation of naphthoquinone in its molten state.

Phthalic acid, benzoic acid or phthalic monoacid as the acid component is admixed with naphthoquinone and each mixture is heated at the temperature higher than each melting point whereby a polycondensation of naphthoquinone occured to give a resinous matter.

That is, when phthalic acid is admixed with pure naphthoquinone at a ratio of 1 wt.%, 3.3 wt.% or 10 wt.%, and each mixture is heated at 135° C., a hardening (apparent hardening from molten liquid) occured after 5.0 hours, 3.3 hours or 2.0 hours, respectively. The similar phenomenone has been found when the other acid component is used instead of phthalic acid.

Benzoic acid is admixed with a highly purified naphthoquinone at a ratio of 1 wt.% (1.3 mole %) or 3 wt.% (3.9 mole %) and the mixture is heated at 135° C.

Figure 1:
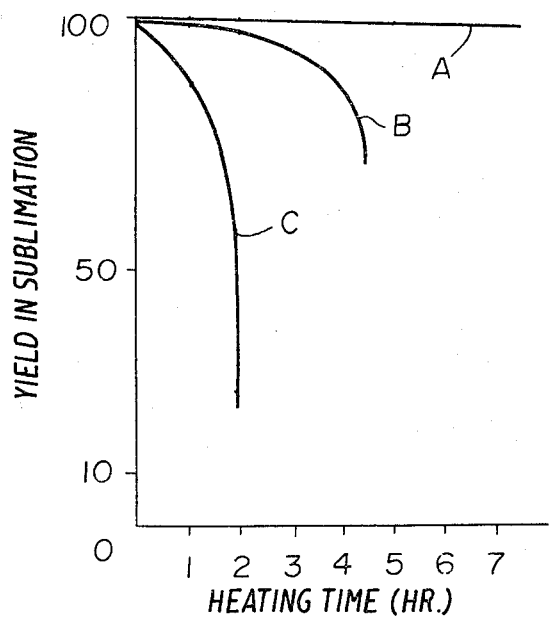
Figure 2:
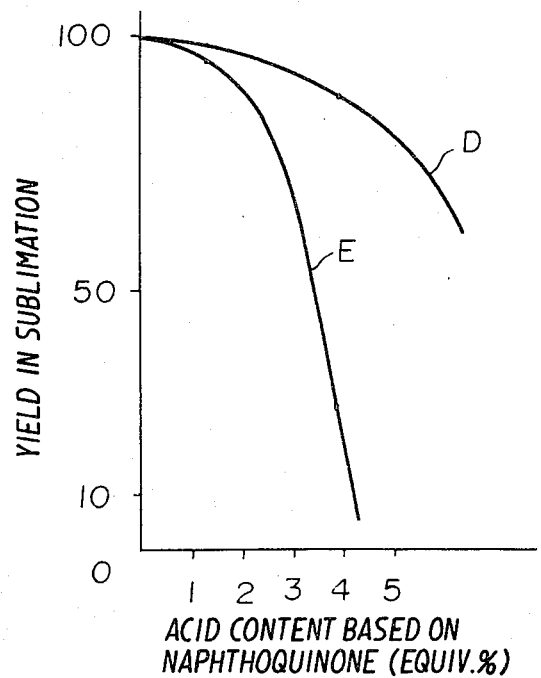

The relation of the heating time to yield of naphthoquinone recovered by sublimation (135° C. for 2 hours) are shown in FIGS. 1 and 2.

In FIG. 1, the yield of naphthoquinone recovered by sublimation (wt.%) is shown on ordinate and the heating time (hours) is shown on abscissa.

Curve A: no addition of benzoic acid
  Curve B: 1 wt.% addition of benzoic acid
  Curve C: 3 wt.% addition of benzoic acid.

FIG. 1 shows the relation of the yield of naphthoquinone recovered by sublimation to the heating time.

FIG. 2 shows effect of yields in sublimation corresponding to contents of benzoic acid as curve D for 1 hour heating and curve E for 2 hour heating which are obtained by connecting points on the curves A, B and C for 1 hour heating and 2 hour heating in FIG. 1.

In FIG. 2, all of points for more than 5 mole % of benzoic acid based on naphthoquinone are outside the curve E. Accordingly, when they are heated at 135° C., the polycondensation of naphthoquinone is rapidly performed to cause zero of yield in sublimation within 2 hours.

As the result, it is clearly understandable that the content of acid components in the crude naphthoquinone is preferably less than 5 equivalent % preferably less than 3 equivalent % most preferably less than about 1 equivalent % calculated as a monobasic acid, based on naphthoquinone.

When the acid component is remained higher than 5 equivalent % calculated as monobasic acid in the crude naphthoquinone, it is necessary to wash the crude naphthoquinone with hot water or a basic aqueous solution of a base such as sodium carbonate, sodium bicarbonate and disodium phthalate to remove the acid component to less than 5 equivalent % in order to distill the crude naphthoquinone.

When the content of the acid component is from 3 equivalent % to 5 equivalent % in the crude naphthoquinone, it is sometimes necessary to carry out the reduced pressure distillation under controlling the temperature of the distillation still near the melting point of the crude naphthoquinone or by a special method such as thin layer instantaneous distillation.

The crude naphthoquinone obtained by the following method can be used for the reduced pressure distillation of the present invention without further treatment. That is, the reaction mixture gas obtained by the catalytic vapor phase oxidation of naphthalene is contacted with an aqueous medium and naphthoquinone was extracted from the resulting mixture of naphthoquinone, phthalic acid and maleic acid, with an aromatic hydrocarbon such as benzene, toluene or xylene.

After washing of the organic layer with a hot water or an aqueous weak alkaline solution, the solvent is evaporated off to give a crude naphthoquinone whose purity is usually from 90 to 97%. In this crude naphthoquinone, a phthalic acid is contained from 0.3 to 1.5% (hot water washing); 0.05 to 1.5% (alkaline solution washing), benzoic acid from 0.02 to 0.5% and additionally polycondensed materials like a pitch is contained.

The crude naphthoquinone obtained like this melts from 110° to 125° C.

When the acid components are removed by washing with a hot water. The temperature is preferably in a range of 50° to 95° C. especially 60° to 90° C. and the volumetric ratio of water to a crude naphthoquinone is preferably in a range of 0.5 to 30 preferably 1 to 15.

When the acid components are removed by washing with a weak alkaline aqueous solution, the temperature is preferably in a range of room temperature to 95° C. especially room temperature to 80° C. and the volumetric ratio of water to a crude naphthoquinone is preferably in a range 0.5 to 30 preferably 1 to 15.

There are two methods for removing the acidic components from the crude naphthoquinone. One is to wash a solution of the crude naphthoquinone in an inert solvent with a hot water or a weak alkaline aqueous solution. The other is to wash the crude naphthoquinone with a hot water or a weak alkaline aqueous solution.

In the latter method, the inert solvent is preferably a hydrocarbon especially an aromatic hydrocarbon though the other inert solvents can be also used. The inert solvent is usually the same one used in the oxidation of naphthalene.

The reduced pressure distillation in the purification can be carried out by using a simple distillation apparatus or a distillation apparatus equipped with a rectification column. In the reduced pressure distillation, the temperature of the flask is controlled from its melting point to 160° C. and the degree of reduced pressure from 1 to 16 Torr. When it is higher than 160° C., a velocity of polycondensation of naphthoquinone is too high to perform the distillation. When it is lower than 160° C., the trouble may be prevented and it is preferable to carry out the reduced pressure distillation at lower than 150° C. It is possible to perform the reduced pressure distillation of naphthoquinone under maintaining the temperature of the distillator at lower than 125° C. of the melting point of pure naphthoquinone and maintaining the temperature of the wall at higher than 125° C.

The distillation can be carried out by a batch system or a continuous system such as thin layer distillation system.

When the acid content in the crude naphthoquinone is small, it is possible to continue the distillation by adding new crude naphthoquinone without discharging the bottom.

As described above, this method is a valuable process for producing easily and precisely a highly purified naphthoquinone in high yield by a reduced pressure distillation of a crude naphthoquinone, industrially.

The inventors have further studied to improve the purification of a crude naphthoquinone, especially to find impurities for accelerating the polycondensation from the crude naphthoquinone. As the result, the inventors have found that impurities having hydroxyl group such as hydroquinone type impurities including a reduced form of naphthoquione of naphthohydroquinone and dimers of orthonaphthoquinone such as 1,1'-binaphthyl-3,4,3',4'-diquinhydrone (hereinafter referring to as diquinhydrone) cause polycondensation of naphthoquinone.

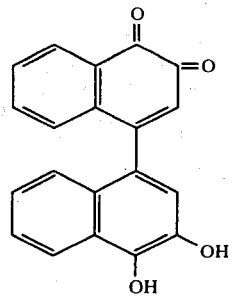

The polycondensation test of naphthoquinone test is carried out by adding such impurity component.

For example, 1 wt.% of naphthohydroquinone is admixed with pure naphthoquinone and its mixture is heated at 135° C. As the result, it is hardened after about 1 hour. On the other hand, 1 wt.% of phthalic acid is admixed with pure naphthoquinone and its mixture is heated at 135° C. As the result, it is hardened after about 5 hours. The results show the fact that the compound having hydroxyl group has stronger characteristic accelerating polycondensation in comparison with the acid component such as phthalic acid.

These hydroquinone impurities having hydroxyl group have relatively small solubility in an aqueous medium whereby it is not easy to separate from the crude naphthoquinone.

In this invention, the hydroquinone type impurities having hydroxyl group are converted to quinone type impurities by an oxidation, in the crude naphthoquinone. When the crude naphthoquinone which is treated to convert the hydroquinone type impurities to the quinone type impurities, is used, the heat stability of a crude naphthoquinone is remarkably improved to attain the present invention.

The oxidizing agents used for oxidizing hydroquinone type impurities in the crude naphthoquinone should be substantially inert to naphthoquinone under the condition but, substantially active to oxidize the hydroquinone type impurities such as naphthohydroxyquinones and diquinhydrones to quinone type impurities.

Suitable oxidizing agents include nitric acid (concentration: less than 60 wt.%); hydrogen peroxide; peracids such as peracetic acid; chlorine water; bromine water; halo-oxyacids such as chloric acid and bromic acid; or salts thereof; ferric chloride, persulfates, chromic acid cupric salts and lead oxide.

The oxidizing methods include a method of contacting with an aqueous solution of an oxidizing agent with a crude naphthoquinone in a medium which does not dissolve naphthoquinone such as water; a method of adding an oxidizing agent in a solution or suspension of a crude naphthoquinone in a medium such as acetone, ether and acetic acid which dissolves naphthoquinone and is miscible to water; and a method of contacting an aqueous solution of an oxidizing agent such as aqueous solution with a solution of a crude naphthoquinone dissolved in a solvent such as benzene, toluene and xylene, which is not miscible to water.

The following method is preferable. The reaction mixture gas obtained by the catalytic vapor phase oxidation of naphthalene is contacted with an aqueous medium and naphthoquinone is extracted from the resulting aqueous mixture of naphthoquinone, phthalic acid and maleic acid with an aromatic hydrocarbon such as benzene, toluene or xylene and the resulting solution of naphthoquinone is washed with a hot water or an aqueous weak alkaline solution and then, contacted with an oxidizing agent such as a dilute nitric acid (concentration: 1 to 60 wt.%). The oxidizing treatment can be carried out before removing the acid components such as phthalic acid by washing with a hot water or an aqueous weak alkaline solution.

An amount of the oxidizing agent can be adjusted by a color change of the powder or the solution of the crude naphthoquinone in the oxidation. The crude naphthoquinone containing the oxidizable impurities such as diquinhydrone is blackish green colored in powder and it is changed to bright yellowish orange color by the oxidation. For example, a xylene solution of the crude naphthoquinone containing the oxidizable impurities such as a xylene solution has dark orange color and it is changed to bright reddish orange color by the oxidation. The oxidizing agent is added to change the color. It is possible to add excess of the oxidizing agent, and it is preferable to add the oxidizing agent at about 1 to 5 times of the amount used for the color change. In the industrial process, suitable amount of the oxidizing agent to the crude naphthoquinone can be estimated. For example, when nitric acid is used as the oxidizing agent, the ratio of the oxidizing agent to naphthoquinone in the crude naphthoquinone is usually in a range of 0.01 to 5 wt.%.

The time for the oxidation depends upon the kind of the oxidizing agent and the treating condition, and it can be estimated by the appearent color change of the crude naphthoquinone as described above.

For example, when the solution of the crude naphthoquinone dissolved in an aromatic hydrocarbon such as benzene is oxidized with nitric acid, it is enough to be shorter than 30 minutes. However, when powdery crude naphthoquinone is suspended in a dilute nitric acid (concentration: a few %) in the oxidation, it may take several hours.

It is preferable to contact a solution of a crude naphthoquinone in an organic solvent with nitric acid having a concentration of 1 to 60% at lower than 95° C. preferably 40° to 70° C. for about 1 to 30 minutes with stirring.

The present invention will be further illustrated by certain examples and references which are provided for purposes of illustration only and are not intended to be limiting the present invention.

EXAMPLE 1

A reaction mixture produced by a catalytic vapor phase oxidation of naphthalene was contacted with water to give an aqueous slurry and the resulting naphthoquinone was extracted with o-xylene. The o-xylene layer was washed with a hot water at 80° C. at a volumetric ratio of 1:1 and o-xylene was distilled off to obtain a crude naphthoquinone having less acid content.

1 Kg of the crude naphthoquinone containing 94 wt.% of naphthoquinone, 0.3 wt.% of phthalic acid, 0.2 wt.% of benzoic acid, 3 wt.% of water and 2.5 wt.% of a polycondensed impurities (0.9 equivalent of acid component as monobasic acid based on naphthoquinone) was charged in 2 liter of a round bottom flask equipped with a distillation column having a diameter of 20 mm and a length of 200 mm which was packed with raschig rings and had a thermometer. The flask was held in an oil bath at 140° C. and the temperature of the distillation column was maintained from about 135° to 140° C.

under a reduced pressure of 2 to 4 Torrs. The content in the flask begins to melt from 110° C. and a distillation of naphthoquinone started from about 120° C. and the temperature of the content was kept between 130° C. and 132° C. and the distillation was smoothly continued. When the temperature elevated to 140° C., a distillation was substantially finished. Total time for the distillation was about 4 hours. The resulting naphthoquinone had bright yellow color.

An amount of the distillate was 852 g, and a purity of naphthoquinone measured by an iodometry was 99.5% and a yield of the distillation based on naphthoquinone in the starting material was 90.2%.

EXAMPLE 2

A crude naphthoquinone containing 91.5 wt.% of naphthoquinone, 2.7 wt.% of phthalic acid and 0.01 wt.% of benzoic acid and ther other polycondensed impurities (5.7 equivalent % of acid components as a monobasic acid based on naphthoquinone) was washed with 10 times of a hot water (80° C.) to obtain a crude naphthoquinone containing 96.2 wt.% of naphthoquinone, 0.9 wt.% of phthalic acid, 0.01 wt.% of benzoic acid and the polycondensed impurities (1.8 equivalent % of acid components as a monobasic acid based on naphthoquinone).

In accordance with the process of Example 1, the distillation was carried out. The time required for the distillation was about 2 hours.

An amount of the distillate was 169 g and a purity of naphthoquinone measured by an iodometry was 98.8% and a yield of the distillation based on naphthoquinone in the starting material was 88.9%.

When 1 kg of the crude naphthoquinone which was not washed with the hot water was used in the reduced pressure distillation, the time required for the distillation was 1.5 hours and the yield of the distilled material was about 50% and a purity of naphthoquinone was 97%.

EXAMPLE 3 AND REFERENCE 1

A reaction mixture gas obtained by a catalytic air oxidation of naphthalene was contacted with water to give an aqueous slurry of naphthoquinone and naphthoquinone was extracted with orthoxylene to obtain 25% of solution of naphthoquinone in orthoxylene.

The o-xylene solution of naphthoquinone (1 liter) was washed with 30% nitric acid (5 ml) at 60° C. for 30 minutes. After standing for a while, water layer was separated off from the mixed solution to give an o-xylene solution and o-xylene was evaporated off to obtain a crude naphthoquinone (a).

In a four necked round bottom flask equipped with a distillation column having a diameter of 30 mm and a length of 200 mm, 200 g of the crude naphthoquinone (a) was charged and it was heated between 130° and 135° C. in an oil bath under a reduced pressure of 2 mmHg. The distillation was continued for about 2 hours to obtain the purified naphthoquinone of Example 3.

On the other hand, as a reference, a part of the 25% solution of naphthoquinone in orthoxylene (non-treatment with nitric acid) was heated at 80° C. under a reduced pressure of 20 mmHg to remove the solvent and to obtain a crude naphthoquinone (b).

In accordance with the process of Example 3 except using 200 g of the crude naphthoquinone (b), the distillation was carried out for 2 hours to obtain the purified naphthoquinone of Reference 1.

EXAMPLE 4 AND REFERENCE 2

In accordance with the process of Example 1 each of the crude naphthoquinones (a), (b) shown in Example 3 and Reference 1, was distilled for about 4 hours to obtain purified naphthoquinones of Example 4 and Reference 2.

The results of Examples 3 and 4 and References 1 and 2 are shown in Table 1.

TABLE 1

|  | Example | | Reference | |
| --- | --- | --- | --- | --- |
|  | 3 | 4 | 1 | 2 |
|  | (oxidation) | | (non-oxidation) | |
| Crude naphthoquinone | | | | |
| Kind | | | | |
| Component | | | | |
| Purity (%) | 95.7 | 95.7 | 94.5 | 94.5 |
| Phthalic acid (%) | 0.5 | 0.5 | 0.5 | 0.5 |
| Benzoic acid (%) | 0.05 | 0.05 | 0.05 | 0.05 |
| Distillation time (hrs) | 2 | 4 | 2 | 4 |
| Recovery rate (%) | 90.0 | 89.3 | 87.1 | 79.5 |
| Purity (%) | 99.4 | 99.4 | 99.0 | 99.0 |
| Yield to naphthoquinone (%) | 93.5 | 93.5 | 91.2 | 83.3 |

From the results of Table 1, it is clear that, in accordance with the example of the process of the present invention, a highly-purified naphthoquinone having higher purity could be obtained in higher yield than those of References. Moreover, even though the distillation time was prolonged by a scale up in the distillation, the yield was not reduced. This is significantly advantageous from the industrial viewpoint.

EXAMPLE 5

6.0 Liters of 25% solution of naphthoquinone in o-xylene obtained by the process of Example 1 was stirred at 60° C. and 3 ml of about 20% nitric acid was added, whereby the dark brown color of the solution was changed to transparent reddish brown after about 2 to 3 minutes and the mixture was further stirred for 20 minutes and kept in stand-still and the lower phase was separated. The solvent was separated from the solution of naphthoquinone in orthoxylene as the upper phase to obtain a crude naphthoquinone containing 94 wt.% of naphthoquinone, 0.3 wt.% of phthalic acid, 0.1 wt.% of benzoic acid and the other polycondensed impurities.

In the flask of Example 1, 1 kg of the crude naphthoquinone was charged and distilled at 130° to 132° C. under a reduced pressure of 2 to 4 mmHg and the distillation was stopped at 140° C. The distillation time was about 4 hours.

An amount of the distillate was 905 g and a purity of naphthoquinone was 99.8%, the color was bright yellow; the yield of the distillation based on naphthoquinone in the starting material was 96.2%.

EXAMPLE 6 AND 7 AND REFERENCE 3

Phthalic anhydride in the reaction mixture gas obtained by a catalytic vapor phase oxidation of naphthalene was condensed and separated and the reaction mixture gas was collected in water to obtain an aqueous slurry of naphthoquinone and naphthoquinone was separated and washed with a hot water to separate a water soluble acid components such as phthalic acid and it was dried to obtain a crude naphthoquinone (c) which contained 94.7 wt.% of naphthoquinone 0.9 wt.% of phthalic acid, 0.06 wt.% of benzoic acid and the other polycondensed impurities.

250 Grams of the powdery crude naphthoquinone (c) was dissolved in 750 g of o-xylene and 2 g of 30% nitric acid was added and the mixture was stirred at 60° C. for 10 minutes and the water phase was separated. Orthoxylene was distilled off from the solution of naphthoquinone in orthoxylene at 80° C. under a reduced pressure of 100 to 120 mmHg. The resulting yellowish brown naphthoquinone was charged in a 1 liter flask and distilled at 130° to 135° C. (oil bath: 135° to 150° C.) under a reduced pressure of 2 to 4 mmHg for about 2.5 hours to obtain 231 g of a purified naphthoquinone of Example 6.

250 Grams of the powdery crude naphthoquinone (c) was added to 400 g of 2.8% nitric acid and the mixture was stirred at 50° to 60° C. for about 3 hours. When the color of the slurry was changed from dark green to yellowish brown, the mixture was filtered and washed with water and dried. The resulting crude naphthoquinone was distilled under a reduced pressure to obtain 228 g of purified naphthoquinone of Example 7.

As the reference, 250 g of the powdery crude naphthoquinone (c) was distilled by the process of Example 6 without carrying out any oxidation of Example 6 or 7 to obtain 157 g of purified naphthoquinone of Reference 3.

The results are shown in Table 2.

TABLE 2

| | Example | | |
|---|---|---|---|
| | 6 | 7 | Reference 3 |
| Crude naphthoquinone Kind | Solution oxidation | Powder oxidation | No oxidation |
| Purified naphthoquinone Purity (%) | 98.4 | 98.4 | 98.3 |
| Yield to naphthoquinone (%) | 95.9 | 94.7 | 65.2 |

REFERENCE 4

Naphthoquinone was separated from an aqueous slurry of naphthoquinone obtained by the process of Example 6, and washed with water and dried to obtain a crude naphthoquinone.

400 Grams of 2% nitric acid was added to 250 g of the powdery crude naphthoquinone and the slurry was stirred at 50° to 60° C. to change color from dark green to yellowish brown. The slurry was filtered off to give a crude naphthoquinone which was washed with water and dried. The resulting crude naphthoquinone containing 90 wt.% of naphthoquinone 7 wt.% of phthalic acid and 0.2 wt.% of benzoic acid.

In accordance with the process of Example 6, 200 g of the crude naphthoquinone was distilled under a reduced pressure to obtain 45 g of the distillate having a purity of 97.9 wt.% and having yellowish red color. The other materials were solidified in the flask.

It is clearly found from these results, when an acid content (such as phthalic acid) is more than 5 equivalent % as a monobasic acid based on naphthoquinone in the crude naphthoquinone even though it is obtained by an oxidaion of the impurities, the yield in the reduced pressure distillation is remarkably low and large amount of naphthoquinone is solidified as polycondensed materials, disadvantageously.

EXAMPLE 8

A crude naphthoquinone (naphthoquinone: 94.0%, phthalic acid: 0.3%; bezoic acid: 0.2%) used in Example 1 was washed with an aqueous solution of sodium bicarbonate and then, treated with dil. nitric acid to give a crude naphthoquinone containing 96.0% of naphthoquinone, 0.1% of phthalic acid, and 0.03% of benzoic acid. The crude naphthoquinone obtained (800 gr) like this was distilled in the same way to Example 1 to give 758 gr of naphthoquinone, whose purity is 99.8% by iodometry. The yield based on naphthoquinone in the charged naphthoquinone is 98.5%.

What is claimed is:

1. In a process for purifying crude naphthoquinone obtained by oxidation of naphthalene, the improvement comprising the steps of reducing the acid content of the crude naphthoquinone to less than 5 equivalent percent as a mono-basic acid based on naphthoquinone distilling the acid-reduced naphthoquinone at reduced pressure and recovering purified naphthoquinone as a distillate.

2. A process according to claim 1 wherein the reduced pressure distillation is carried out at a temperature higher than the melting point of the crude naphthoquinone and lower than 160° C.

3. A process according to claim 1 wherein the crude naphthoquinone is treated with an oxidizing agent to oxidize hydroxyl group type impurities in the crude naphthoquinone, before the reduced pressure distillation.

4. A process according to claim 3 wherein the hydroxyl group type impurities are hydroquinone type impurities.

5. A process according to any one of claims 1, 2, 3 or 4 wherein a crude naphthoquinone is washed with a hot water or an alkaline solution to remove phthalic acid and benzoic acid.

6. A process according to claim 3 wherein the oxidation of the impurities in a crude naphthoquinone is carried out before reduction of the acid content.

7. A process according to claim 3 wherein the oxidizing agent is substantially inert to naphthoquinone under the oxidization conditions but substantially active to oxidize hydroxyl group type impurities.

8. A process according to claim 7 wherein the oxidizing agent is nitric acid and a crude naphthoquinone is in powder form or in solution in an aromatic hydrocarbon.

9. A process according to claim 3, wherein the oxidation of the impurities in the crude naphthoquinone is carried out after reduction of the acid content.

* * * * *